(12) United States Patent
Benjamin et al.

(10) Patent No.: US 7,200,858 B1
(45) Date of Patent: Apr. 3, 2007

(54) DATA DISTRIBUTION SYSTEM

(75) Inventors: Menashe Benjamin, Raanana (IL); Michael Elad, Haifa (IL); Ran Bar-Sella, Haifa (IL); Yosef Reichman, Kfar Saba (IL); Jacob Margolin, Ramat-Gan (IL)

(73) Assignee: Algotec Systems Ltd., Raanana (IL)

( * ) Notice: Subject to any disclaimer, the term of this patent is extended or adjusted under 35 U.S.C. 154(b) by 0 days.

(21) Appl. No.: 09/300,490

(22) Filed: Apr. 28, 1999

Related U.S. Application Data (63) Continuation of application No. PCT/IL97/00349, filed on Oct. 29, 1997.

(30) Foreign Application Priority Data

Oct. 30, 1996 (IL) .................................... 119523

(51) Int. Cl.
  H04N 1/173 (2006.01)
  G06F 17/30 (2006.01)
(52) U.S. Cl. .................. 725/90; 725/132; 725/140; 375/240.02; 375/240.23
(58) Field of Classification Search ................ 725/37, 725/90, 140; 382/240; 375/240.12, 240.02, 375/240.23; 348/586
See application file for complete search history.

(56) References Cited

U.S. PATENT DOCUMENTS

| | | | | |
|---|---|---|---|---|
| 5,416,602 A | * | 5/1995 | Inga et al. ................... | 358/403 |
| 5,432,871 A | | 7/1995 | Novik | |
| 5,513,101 A | * | 4/1996 | Pinsky et al. .................. | 705/3 |
| 5,793,435 A | * | 8/1998 | Ward et al. ................. | 348/448 |
| 5,838,906 A | * | 11/1998 | Doyle et al. | |
| 5,845,013 A | * | 12/1998 | Bouchard et al. ........... | 382/242 |
| 5,851,186 A | * | 12/1998 | Wood et al. ................. | 600/437 |
| 5,859,972 A | * | 1/1999 | Subramaniam et al. ..... | 709/203 |
| 5,905,820 A | * | 5/1999 | Cushman et al. ........... | 382/299 |
| 5,911,132 A | * | 6/1999 | Sloane ......................... | 705/3 |
| 5,920,317 A | * | 7/1999 | McDonald ................... | 345/356 |
| 5,949,491 A | * | 9/1999 | Callahan et al. ........... | 348/442 |
| 6,022,315 A | * | 2/2000 | Iliff ............................ | 600/300 |
| 6,052,732 A | * | 4/2000 | Gosling ...................... | 709/229 |
| 6,101,282 A | * | 8/2000 | Hirabayashi et al. ....... | 382/246 |
| 6,115,486 A | | 9/2000 | Cantoni | |
| 6,256,346 B1 | * | 7/2001 | Yamaguchi et al. ... | 375/240.12 |
| 6,266,817 B1 | * | 7/2001 | Chaddha ..................... | 725/146 |
| 6,275,988 B1 | * | 8/2001 | Nagashima et al. .......... | 725/8 |

FOREIGN PATENT DOCUMENTS

WO  WO 9629818  9/1996

OTHER PUBLICATIONS (Amy Cook; Acuson Announces Release 2.6 of Aegis® Digital Image and Data Management System; May 26, 1996; PR Newswire).*

(Continued)

*Primary Examiner*—Chris Kelley
*Assistant Examiner*—Reuben M. Brown
(74) *Attorney, Agent, or Firm*—Ehrlich & Fenster (57) ABSTRACT

An interactive system for obtaining data for diagnostic purposes from a server having access to stores of said data wherein the server supplies the data and software to a data requesting user that enables the user to receive the data progressively so as to decide during the receipt of the data what portions of the data are to be received thereby decreasing the time required to receive the data and that enables the user to load the software to process the supplied data.

48 Claims, 7 Drawing Sheets

OTHER PUBLICATIONS (Brochure; Sequoia 512; 1996; Acuson Corporation).*
(Doyle, et al; Integrated Control of Distributed Volume Visualization Through the World-Wide-Web; Oct. 1994; IEEE; Proceedings of the Visualization).*
(Acuson Demonstrates Power of the Internet for Medical Diagnosis at 1997 RSNA Meeting; Dec. 1, 1997; PR Newswire).*
(Using Netscape 2, Special Edition; Mrak Brown; 1995; Que Corporation; pp. 401-417; 885-907; 969-979).*
(The Java Languge Envirnment, A White Paper; James Gosling; May 1996; Sun Microsystems).*
Hill F. et al. "Interactive Image Query System Using Progressive Transmission" SIGGRAPH '83, Detroit, MI, USA, Jul. 25-29, 1983, vol. 17, No. 3, Computer Graphics, 1983, USA, pp. 323-330.
Bitti M.G. et al: "A WWW-Based Distributed System for Medical Data Analysis and 3D Reconstruction" Proceedings of the International Symposium on Computer & Communication Systems for Image Guided Diagnosis & Therapy, Proceedings of Car'96: Computer Assited Radiology-10th International Symposium Paris, France, Jun. '96.
Xu M et al: Adaptive, segmented attenuation correction for whole-body PET Imaging IEEE Transactions on Nuclear Science, Feb. 1996, IEEE, USA. vol. 43, No. 1, pt 2, pp. 331-336.
Nosratinia A et al: "Interframe Coding of Magnetic Resonance Images" IEEE Transactions on Medical Imaging, vol. 15, No. 5, Oct. 1996, pp. 639-647.

Andresen, D. et al.; "Scalability Issues for High Performance Digital Libraries on the World Wide Web"; Proceedings of the Third Forum on Research and Technology Advances in Washington, DC, US May 13-15, 1996; IEEE Comput Soc, US,; pp. 139-148.
Long, L. R. et al.; "Client/Server Design for Fast Retrieval of Large Images on the Internet"; Computer-Based Medical Systems, Proceedings of the Eighth IEEE Symposium on Lurbock; Jun. 9-10, 1995; IEEE Comput. Soc; pp. 284-291.
Bitti, M.G., et al; "A WWW-Based Distribution System for Medical Data Analysis and 3D Reconstruction"; Proceedings of the International Symposium on Computer and Communication Systems for Image Guided Diagnosis and Therapy; Proceedings of CAR'96:Computer Assisted Radiology-10$^{th}$ International Symposium; Jun. 1996; pp. 345-350.
Hill, F.S. Jr., et al; "Interactive Image Query System using Progressive Transmission"; Computer Graphics; Jul. 1983; vol. 17, No. 17, No. 3; pp. 323-330.
Fowler, J. E. et al.; "Lossless Compression of Volume Data"; appears in Proceedings of the 1994 Symposium on Volume Visualization, (Washington, DC), pp. 43-53; Oct. 1994.
Chiueh, T. et al.; "Integrated Volume Compression and Visualization"; Proceedings of the 8$^{th}$ IEEE Visualization '97 Conference; pp. 329-336.

* cited by examiner

DATA DISTRIBUTION SYSTEM

RELATED APPLICATION

The present application is a continuation of PCT/IL97/00349, filed 29 Oct. 1997, which designated the United States.

FIELD OF THE INVENTION

This invention is concerned with interactive communication systems linking central locations having access to stores of data and images used for medical purposes and a plurality of outlying users of the images and data for medical review, processing, assessment and diagnostics.

BACKGROUND OF THE INVENTION

Modern hospitals and health centers today usually have several computerized systems for medical information gathering, exchange, storage and processing. Herein such a system is referred to as a "data source". Medical information may come in textual, voice, sound, graphical, and image modalities. Such medical information may be required by authorized personnel, including those located outside the hospital premises, and equipped with computers of some sort. Herein the requiring side is referred to as the "user". In present systems the users are equipped with their own software to access the data source. Difficulties in the use of such computerized systems are caused by such things as the varied networking procedures required to fetch the data, the lack of an industry standard, the lack of an easy to use user interface and, in the case of image data transfer, the channel bandwidth requirements along with the typically large volumes of the image information, which in turn translates into very long transmission periods. In addition to that, a typical user might be required to master the skills of operating a large number of software systems like those used with various data processors, the varied communication software, software installations procedures, etc. The system administrator needs to install the different types of application software in large numbers of computers, and update this software, in each computer, every time a new version is used. This proliferation of software and hardware in the medical data processing systems make such systems difficult to maintain and a burden to update.

Presently, more and more hospitals and clinics are uniting for economic reasons to form healthcare enterprises with consolidated resources, having a single headquarters for managing the organization. The consolidation of resources also takes place inside individual hospitals, with the primary goal of facilitating data exchanges inside the hospital, with hospital personnel outside the hospital premises, as well as with other related facilities and with the enterprise headquarters. Generally, most individual facilities that make up the enterprise operate special systems to store and manage various parts of their clinical data. One can generally view these systems as being composed of data acquisition devices, data storage devices (data banks), and data management and communication modules. The users are connected to the data banks via various networking procedures and communications protocols. These users may operate a variety of computer hardware systems. Access of each user to stored patient data is presently done through the use of special application software on the user's computer. Since presently, most health and medical organizations have constructed their information systems and communications network over a period of time, access to these systems is often complicated, and sometimes requires the user to master several application, software and communication protocols. Typically, no common access method or user interface is available to the user, and users are often confined to the use of particular hardware at a specific location to access the data. The need to access image data further complicates the situation. The large bandwidth required from the communications link, the large data volumes, and the special processing that is usually needed, often requires the use of special software and hardware on the user's side.

Thus, one problem encountered with the present server-user communication systems for transferring medical data is the many different interfaces, software applications, and communication protocols required and the many different types of work stations that make up the "installed base". Due to this proliferation of different work stations requiring different software applications, interfaces and communications protocols, then whenever a new improved system or a new data type become available, the many different work stations have to be equipped with the software for utilizing the new systems or data. This is not only expensive, but time consuming in that the installation of the software in each of the many different work stations and the central server requires time and usually requires expertise beyond that of the doctor or medical professional using the workstation.

A second and equally troublesome problem is encountered when the data requested by the user includes images that must be transmitted over a given enterprise network. This is due to the long time required for transmitting image data as compared to other forms of data. Image compression is used to reduce transmission times. For clinical image data, special precautions must be taken if lossy compression is implemented, due to the potential loss of possibly vital findings. Lossless compression schemes are therefore employed, which provide a relatively small reduction of image transmission time (a factor of 2–3 for radiology images). Interactive compression schemes, that optimize the transmission time for any given user and user type are currently not available in existing healthcare information systems. Such an interactive compression scheme is presented as part of this invention.

Figure 1:
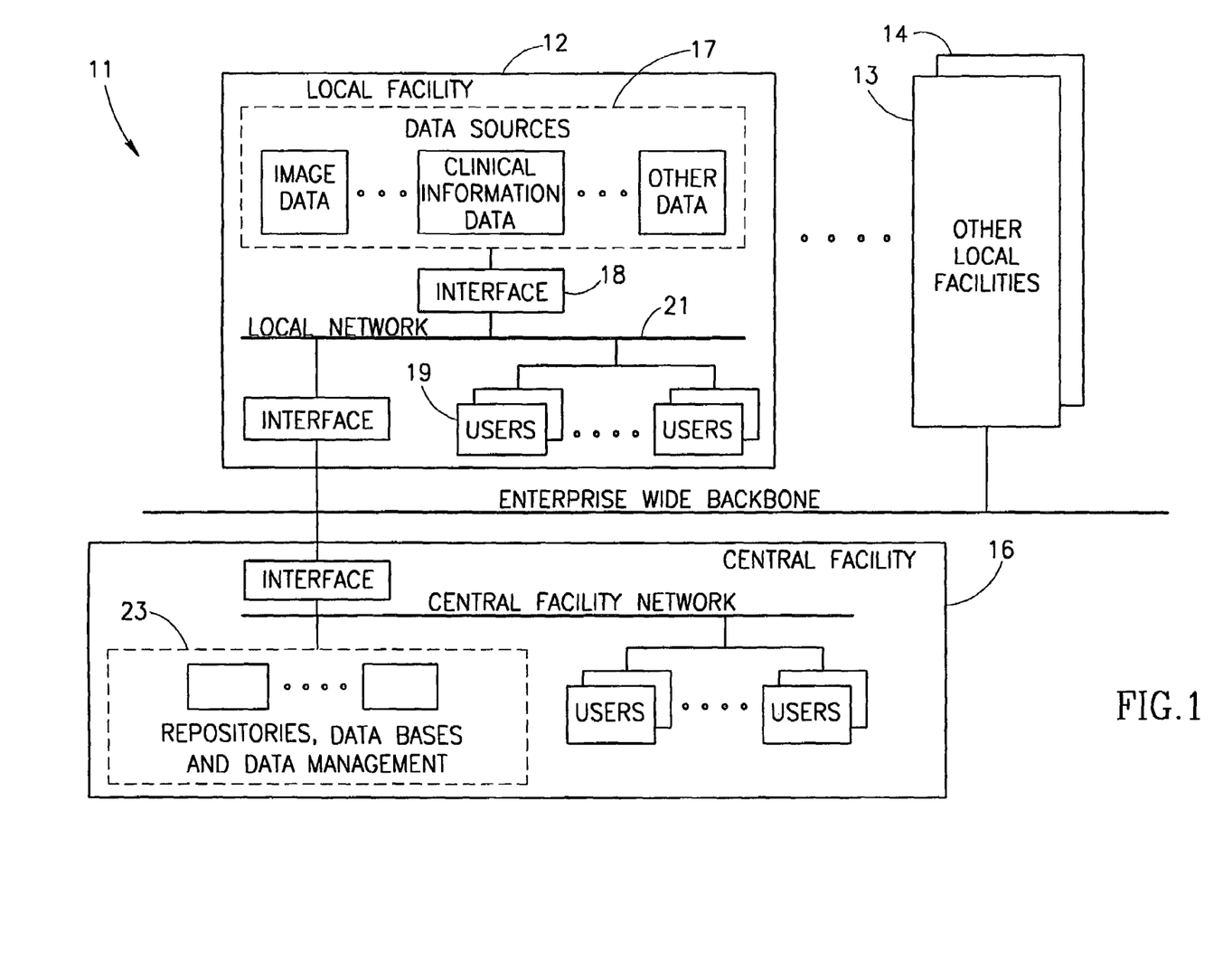
FIG. 1—is a conceptual representation of a present prior art enterprise wide healthcare information system, FIG. 2—adds data distribution servers to the enterprise healthcare information system to facilitate enterprise wide data transfer, FIG. 3—presents a logical representation of the data distribution server concept of FIG. 2.

The above can be summarized in a conceptual diagram (FIG. 1). An enterprise wide healthcare information system 11 may be conceptually conceived as comprising several local facilities, 12–14, connected to a central facility 16. Each local facility comprises data sources 17 connected through appropriate interfaces such as interface 18, to the local network, to which the various local users 19 are connected too. The local network of each local facility is in turn connected to the central facility through another interface (possibly including firewalls and security features). The central facility comprises a similar structure, with the addition of central repositories 23, data bases, and data management tools. This structure of the presently available systems suffers from the problems described above. Thus those skilled in the art are still searching for effective solution to the existing problems.

BRIEF DESCRIPTION OF THE INVENTION

Figure 2:
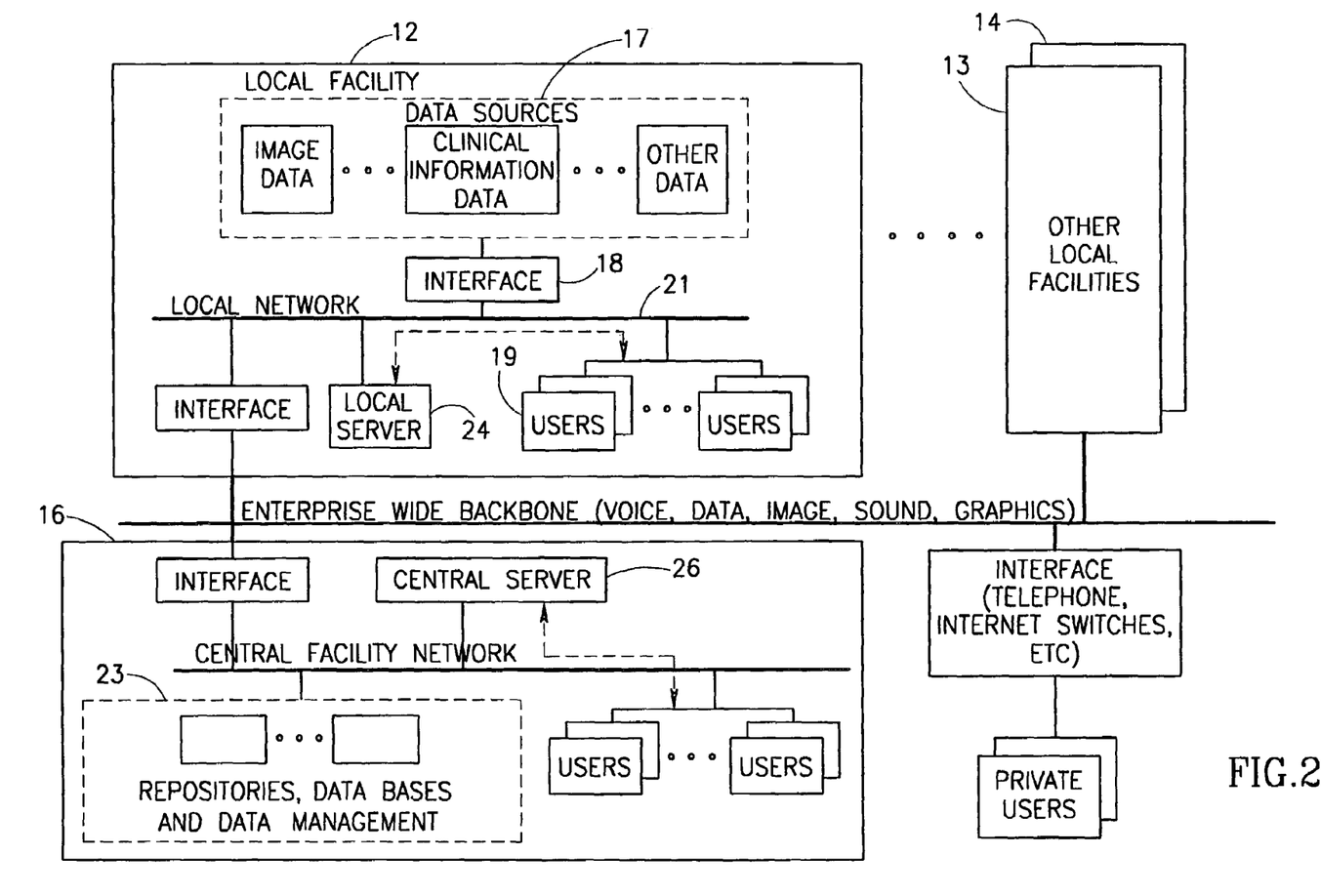
Figure 3:
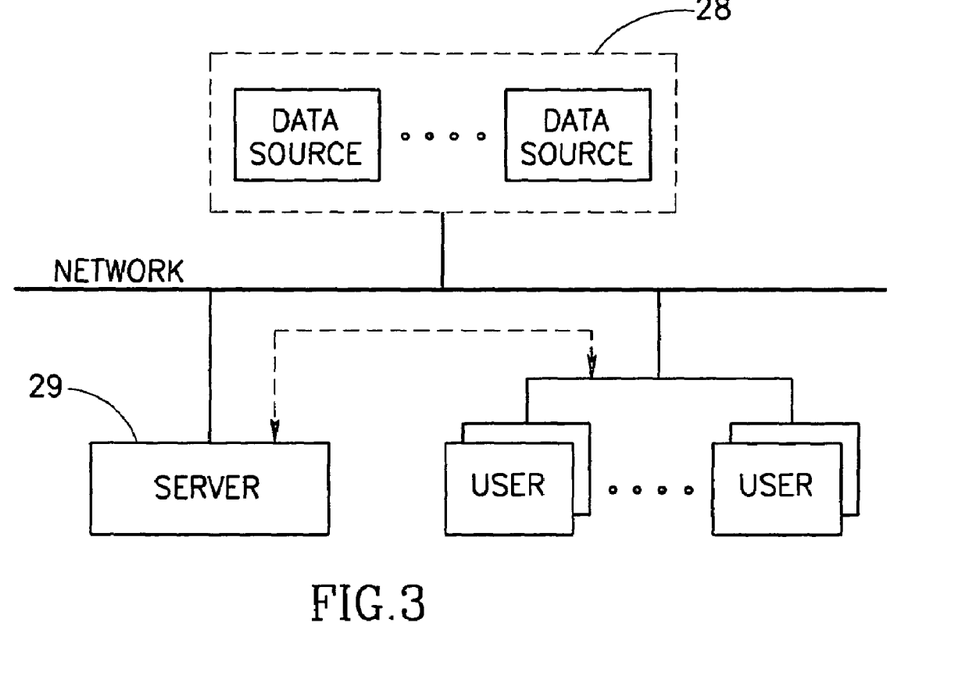

This invention provides systems and methods for largely overcoming the above problems, among other things, by adding data distribution servers, such as local server 24 and central server 26 as indicated in FIG. 2. The concept detailed in FIG. 2 is logically summarized in FIG. 3. The various clinical data acquisition devices and data banks are conceptually grouped into a "data source" block 28. A server 29 is introduced as an intermediate level between the data source and the users. The introduction of the server, with the appropriate functionality and data handling algorithms, alleviates many of the problems presented above.

While the concept and method introduced here is applicable for the distribution of any type of clinical and non-clinical information, this invention will focus on solving the problem of distributing clinical images over the network, which poses one of the major obstacles in implementing a complete and comprehensive healthcare clinical information system.

The present medical image data communications and networking system overcomes the above described and other problems by providing an interactive and efficient method for a user to obtain images for diagnostic, review and processing purposes from a server having access to a plurality of stored images. The method comprises the following steps:

connecting a user's computer to a server over a communications networks, interfacing the computer and the user (e.g. installing an industry standard browser software, such as Netscape, Explorer, etc., on the user's computer), using a program in the server to receive from the server special software (applet) for the user's computer necessary for data selection and processing, selecting data for transmission from the server to the user's computer, compressing the data for transmission by selectively using either lossy or loss-less compression algorithms, progressively transmitting the requested data over the network, receiving and decompressing the compressed data using the applet and producing preview images of progressively improving resolution, and using the preview images for selecting parts or a subset of the images for continued transmission to reduce the required transmission time.

The above enumerated and other problems are overcome, by using, for example, the Internet to connect the user and the server. The user's computer does not need any software for receiving or processing the requested image except the standard browser software. Instead, the necessary software is transmitted from the server along with the image using a network computing language such as Java or ActiveX or similar language. Accordingly, if and when there are changes or improvements made in the data, the software or the image processing procedure, it is no longer required for a technician to go and install the necessary software or modify the existing software on each user's computer. Instead this is accomplished using the Java or ActiveX type language.

The second problem, that is the time required for transmitting of images is overcome by progressively sending "layers" of the data so as to make preview images which are not necessarily of high resolution quality, but as more and more layers of data are sent the resolution progressively improves. The user will be able to decide to get only a certain portion (Region of Interest—ROI) of the image rather than the whole image, or to entirely discard the image by stopping the transmission. In addition, based on the preview images, the user may decide to request only a subset of an image set. Further time savings result from using segmentation whereby background in the image is automatically detected and omitted. Also, a lossy compression can be used for the preview image, and upgrading to full resolution and quality can be done on specific request. Therefore, in the process of image viewing, much less data may be transmitted than in the present systems and time savings can be considerable. This greatly alleviates the problem faced when transmitting clinical images from a server to a user for diagnostic purposes.

Hence, the system described herein overcomes the above mentioned difficulties by applying a coding scheme which includes lossy and loss-less algorithms, with pyramidal structuring of the images for progressive transmission. A simple yet general man to machine interface (MMI) enables the user to activate the compression algorithms interactively, according to on-line requirements. Today's network computing software (such as Java or ActiveX) enable a simple procedure by which the user's software is installed by a networking service program on the server, and there is no installation requiring user intervention on the user side (except a one time installation of an industry standard browser software).

A sample compression-decompression scheme for the treated images to be used on a wide range of communication networks is presented. This scheme can treat both volumes (group of images) and single images applying loss-less or lossy coding, according to requirements posed by the user and the available resources. A progressive approach is applied within the compression-decompression scheme, which enables the user to get previews or overviews of the transmitted image long prior to the time required to transmit the entire image. The quality of the overviews improves over time thus enabling the user to get basic impressions of the transmitted data long before the entire image has arrived. The basic impressions enable the user to interact with the server so that only the actually necessary data is really sent to the user. A typical session of requesting a medical image from a medical image store involves a series of decisions regarding image and region of interest selection. The progressive, interactive approach enables the user to make many of these decisions before the entire image-set is received. This further reduces the time required to get the needed images and improves the resource utilization by transmitting, in full description, only that part of the data which is really of interest.

The compression-decompression scheme is designed to be asymmetric, namely, the computational requirements on the server/coding side are much greater compared to the requirements on the user/decoding side. This is in accordance with the assumption that the server's side of the system is implemented on a relatively powerful computer while the user's hardware requirements are minimal (the user's work station can also be a simple Personal Computer).

The coding scheme described herein utilizes various properties of the typical medical images, for coding benefit. Medical images often contain an informative part surrounded by a background which is of less medical importance. The proposed coding scheme takes advantage of this particular image structure by using segmentation of the image prior to transmission, in order to avoid transmitting the information-less background. The background information is coded and transmitted only upon a specific user's request and/or after the informative part of the images has arrived at the user.

Medical images are typically acquired using more than 8 bits per pixel. Many if not most of potential users are only able to display color or gray level information at 8 bits per pixel. For that reason a lossy version of the image can be obtained by dynamic range reduction using simple well known techniques generally referred to as "windowing", or more complicated adaptive techniques, such as adaptive "windowing". Those lossy image versions are much smaller in size than the original image and can be transmitted relatively fast, enabling the user to display a lossy version of the image in a short time. This lossy version serves as a preview or overview image and also as a basis for further improvements of image quality. As an overview image it enables the user to decide what part of the image set and image region is really required. The interactive nature of the user/server protocol enables the client to dynamically specify which part of the image set is needed. Only the needed part will be fully transmitted; thus, reducing the required transmission periods.

Because of the progressive nature of the coding schemes, the images at the user's side are available for on-line processing during transmission. Various enhancement, display, and analysis techniques are supported. Interactive graphics on the user's side enables the viewer to define a region of interest in order to confine the transmission to that specific area.

It should be understood that, in a preferred embodiment, the interactive communication system also interfaces to clinical information systems available to the server enabling the transfer of data that includes, for example, medical reports, medical history, laboratory results and test results.

There is therefore provided in accordance with a preferred embodiment of the invention, an interactive method for allowing a user to obtain image data for diagnostic purposes from a server having access to stored data, comprising:

connecting a user's computer to the server over a communication network;

receiving from the server image reconstruction software for the user's computer;

requesting specific image data for transmission from the server to the user's computer;

progressively transmitting the requested specific image data over the network from the server to user's computer; and reconstructing a diagnostic quality image, from the image data, using the reconstruction software.

Preferably, the method comprises image processing said reconstructed image using said reconstruction software. Alternatively or additionally, the method comprises:

receiving from the server image selection software for the user's computer, wherein said image selection software is used for said requesting. Preferably, said image selection software controls the transmission of the image data.

Alternatively or additionally, said image selection software displays images from said server. Alternatively or additionally, said image selection software and said reconstruction software are received together. Alternatively or additionally, said image selection software and said reconstruction software comprise a single software unit. Alternatively or additionally, said image selection software is operative to stop the transmission of the data. Preferably, said image selection software is operative to restart the transmission of the data, after said stopping.

In a preferred embodiment of the invention, said image selection software controls processing of data at said server, prior to its transmission. Preferably, said processing comprises reducing said data from a large bit-per-pixel ratio to a small bit per pixel ratio.

Alternatively or additionally, said image selection software controls said server to selectively transmit only portions of the image data. Alternatively or additionally, the method comprises interactively providing user input to said image selection software, to affect said control.

Alternatively or additionally, the image selection software comprises application software coded using a device independent network programming language.

Alternatively or additionally, the reconstruction software comprises application software coded using a device independent network programming language.

Preferably, said language comprises Java. Alternatively, said language comprises ActiveX.

In a preferred embodiment of the invention, reconstructing comprises:

reconstructing images of progressively improving quality from the progressively received data;

using the produced improved images of progressively produced quality to decide on processing of the images; and processing said images, prior to the progressively received data being completely received.

Alternatively or additionally, reconstructing comprises:

reconstructing images of progressively improving quality from the progressively received data;

using the produced improved images of progressively produced quality to decide on processing of the images; and interactively selecting regions of interests in the images based on said progressively improved images, prior to the progressively received data being completely received.

There is also provided in accordance with a preferred embodiment of the invention, an interactive method for allowing a user to obtain image data for diagnostic purposes from a server having access to stored data, comprising:

connecting a user's computer to the server over a communication network;

requesting specific image data for transmission from the server to the user's computer;

progressively transmitting the requested specific data over the network to the user's computer;

reconstructing images of progressively improving quality from the progressively received data;

using the produced images of progressively produced quality to decide on processing of the images; and processing said images, prior to the progressively received data being completely received.

There is also provided in accordance with a preferred embodiment of the invention, an interactive method for allowing a user to obtain image data for diagnostic purposes from a server having access to stored data, comprising:

connecting a user's computer to the server over a communication network;

requesting specific image data for transmission from the server to the user's computer;

progressively transmitting the requested specific data over the network to the user's computer;

reconstructing images of progressively improving quality from the progressively received data;

using the produced improved images of progressively produced quality to decide on processing of the images; and interactively selecting regions of interests in the images based on said progressively improved images, prior to the progressively received data being completely received.

In a preferred embodiment of the invention, said image data represents a set of images and wherein said using the produced images to decide comprises using the produced images to decide on processing images which have not yet been received.

In a preferred embodiment of the invention, the method comprises deciding on a termination of transmission of said progressive image data, responsive to said reconstructed images. Alternatively or additionally, said processing comprises converting said image data to image data representing an image with fewer bits per pixel. Alternatively or additionally, said processing comprises selecting a region of interest of said images. Alternatively or additionally, said processing said images is performed on said image data, at said server, prior to their being transmitted to said user's computer.

There is also provided in accordance with a preferred embodiment of the invention, an interactive method for allowing a user to obtain data for diagnostic purposes from a server having access to stored data, said method comprising:

connecting a user's computer to the server over a communication network;

receiving from the server reconstruction software for the user's computer;

requesting specific data for transmission from the server to the user's computer;

progressively transmitting the requested specific data over the network;

progressively receiving the data using the reconstruction software to process the received data and produce images of progressively improving quality; and using the produced progressively improved images to decide on further transmission of the image data.

There is also provided in accordance with a preferred embodiment of the invention, an interactive method for allowing a user to obtain image data for diagnostic purposes from a server having access to stored data, comprising:

connecting a user's computer to the server over a communication network;

requesting specific image data for transmission from the server to the user's computer;

reducing the bit-per-pixel ratio of parts of the data being transmitted, responsive to said request; and transmitting the reduced data.

Preferably, said reduction in bit-per-pixel ratio is performed responsive to user input at said user's computer. Preferably, said user input comprises selection of an image portion.

In a preferred embodiment of the invention, reducing the bit-per-pixel ratio comprises:

calculating an average "M" of the gray values in the image and a standard deviation "S" of said gray values; and rescaling these values in the range [(M−S/2) ... (M+S/2)] to obtain a new lower number of bits per pixel.

Alternatively, reducing the bit-per-pixel ratio comprises:

estimating the mean and standard deviation of the gray levels locally; and resealing these values to obtain a new lower number of bits per pixel.

In a preferred embodiment of the invention, progressively transmitting the requested data over the network comprises:

recomposing the image into a pyramidal structure comprised of layers, said layers ranging sequentially from a layer having the least amount of data to a layer having the most data; and transmitting the layers making up the pyramid individually starting with the layer with the least amount of data to enable the user to view the progressively improving image to decide on further transmission of the image.

Preferably, recomposing the image into a pyramidal structure comprises reducing the image to provide the different layers at the transmitting end for progressive transmittal.

Preferably, reducing comprises discarding alternate rows and columns to create an image that is a quarter of the size of the original image.

In a preferred embodiment of the invention, the method comprises:

providing a first layer with reduced resolution in the pyramidal structure;

providing remaining layers that contain residual values with increased resolution; and progressively receiving the data using to provide images based on the received data of progressively improved resolution.

In a preferred embodiment of the invention, the method comprises:

compressing the requested data transmitted over the network; and decompressing the received required data to provide images.

Preferably, compressing comprises spatially decorrelating the data by predicting each pixel at the current resolution using its spatial casual neighbors. Alternatively, compressing comprises temporally decorrelating each pixel by predicting each pixel value at the current resolution using the values of temporal neighbors from previous images. Preferably, a predictor X used in predicting each pixel for a single image is equal to f(a, b, c), where a, b and c are previously predicted neighboring pixels.

Alternatively, a predictor X used in predicting each pixel for a group of images equals f(a, b, c, a1, b1, c1, x1) where a, b and c are previously predicted neighboring pixels in a same image and a1, b1, c1 and x1 are corresponding pixels in a previously predicted image of the image group.

In a preferred embodiment of the invention, said compressing and said decompressing use entropy coding and decoding respectively. Preferably, said entropy coding and decoding are accomplished using Golomb Rice entropy coding and decoding.

In a preferred embodiment of the invention, the method comprises using adaptive slicing and entropy coding and decoding of each slice for progressively transmitting the requested specific image data, wherein said entropy coding generates a residual matrix.

Preferably, using adaptive slicing comprises:

scanning the obtained residual matrix into a residual vector; and partitioning the residual vector into variable length sub vectors with a relatively homogeneous probability distribution function.

Preferably, partitioning comprises:

estimating the local mean and variance on the sub-vector;

sectioning the vector on high transients; and coding each sub vector separately.

Alternatively or additionally, said compression does not increase the size of said data.

In a preferred embodiment of the invention, connecting the user computer to the server over a communication network comprises connecting over the Internet. Alternatively, connecting the user computer to the server over a communication network comprises using a dial up communication system. Alternatively, connecting the user computer to the server over the communication network comprises using networking facilities.

Alternatively or additionally, the stored data comprises data for a plurality of "postage stamp" images. Preferably, the method comprises using "postage stamp" images as a catalog for selecting those images for which no further data is to be transmitted and those images for which further data is to be transmitted. Alternatively or additionally, said postage stamps comprise a lowest level in a pyramidal representation of said images.

In a preferred embodiment of the invention, the method comprises stopping the transmission at the user's request. Preferably, the method comprises restarting the transmission at the user's request.

In a preferred embodiment of the invention, progressively transmitting comprising serially transmitting a sequence of images. Alternatively or additionally, progressively transmitting comprising transmitting data operative to reconstruct images of increasing resolution.

In a preferred embodiment of the invention, progressively transmitting the requested data over the network comprises segmenting an image into background parts and tissue parts, and transmitting the tissue parts first.

There is also provided in accordance with a preferred embodiment of the invention, an interactive method for allowing a user to obtain image data for diagnostic purposes from a server having access to stored data, comprising:

connecting a user's computer to the server over a communication network;

segmenting an image into background parts and tissue parts; and transmitting the tissue parts first.

Preferably, the method comprises requesting said specific image data for transmission from the server to the user's computer.

In a preferred embodiment of the invention, the method comprises stopping the transmission before transmitting the background part. Alternatively, the method comprises transmitting the background part to achieve loss-less transmission of the image.

There is also provided in accordance with a preferred embodiment of the invention, a method of adaptive slice compression, for compressing progressively transmitted multi-slice image data, which data is progressively transmitted as pyramid layers, comprising encoding said data using entropy encoding, which encoding generates a residual matrix;

scanning the obtained residual matrix into a vector; and partitioning the residual vector into variable length sub vectors with a relatively homogeneous probability distribution function.

Preferably, partitioning comprises:

estimating the local mean and variance on the vector;

sectioning the vector on high transients; and coding each sub vector separately.

There is also provided in accordance with a preferred embodiment of the invention, an interactive method for allowing a user to obtain image data for diagnostic purposes from a server having access to stored data, comprising:

connecting a user's computer to the server over a communication network;

requesting specific image data for transmission from the server to the user's computer;

transmitting the requested specific image data over the network from the server to user's computer;

stopping said transmission, by command from a user at said user's computer; and continuing said transmission after a time, on command from said user.

Preferably, said continued transmission is modified by said user, responsive to images reconstructed from said stopped transmission. Alternatively or additionally, stopping said transmission stops compression of images at said server. Alternatively or additionally, stopping said transmission comprises stopping said transmission after a partial-resolution representation of the image data is transmitted.

There is also provided in accordance with a preferred embodiment of the invention, an interactive method for allowing a user to obtain image data for diagnostic purposes from a server having access to stored data, comprising:

connecting a user's computer to the server over a communication network;

receiving from the server image reconstruction software for the user's computer;

requesting specific image data for transmission from the server to the user's computer;

transmitting the requested specific image data over the network from the server to user's computer; and reconstructing a diagnostic quality image, from the image data, using the reconstruction software.

BRIEF DESCRIPTION OF THE DRAWINGS

For a more complete understanding of the invention, reference should be made to the following detailed description which is given in conjunction with the accompanying drawings, of which.

GENERAL DESCRIPTION OF THE PREFERRED EMBODIMENT

1. System Overview

The system consists of a server that has access to data banks and distributes the data on demand. Several users can connect, simultaneously, to the server, over communication lines. In this system the server is also responsible for image pre-processing and for distributing user software. The user's function is to manage the medical image acquisition and processing through the use of an intuitive Man-Machine Interface, a special protocol and the available hardware and communication resources.

A typical medical image acquisition session will start by a simple data request, made by the user, to the system's server communication site. This generic request can be accomplished using any of standard communication protocols and, for example, through an HTTP (Hyper Text Transmission Protocol) connection to the server (which can be designed for access purposes as a Web (WWW) site. There are no requirements on the user's hardware and browser software other than the basic capability to communicate over the chosen communication line and for the browser to support a network computing language such as Java or ActiveX. Using the Web, these requirements will include a link to the Internet and a standard Web browser as described above. Upon such a request, the server will download, to the user's machine, a network application applet. This network application will serve as the user's application in all future interactions with the server. The network application is a generic, platform independent application written in a suitable network application language such as, but not limited to, Java or ActiveX. The network language may also be any other software that utilizes the communication capabilities of the user's machine. After a short authorization and authentication procedure, the user will be presented with an opportunity to request medical data. The communication can also be accomplished using "dial-up" or other "networking" schemes.

Medical data includes Medical Image Data, throughout this description. It may comprise a number of medical images, of various modalities, which are available for transmission through the server. The user may define the specific medical case of interest through the use of network application queries into the server's database. Selecting the case is done using case identifiers which are usually, but not limited to, textual, image icons, etc. A typical CT (Computerized Tomography) case may contain 50–100 medical images. The actual transmission of the medical image information is accomplished through the use of a compression/decompression algorithm and a powerful client/server protocol. The transmission is relatively fast owing to a smart utilization of the available hardware and network resources and focusing on the needed medical information by providing the user with interim information, thus letting the user refine the information query parameters during the acquisition process itself. The compression-decompression algorithm is basic to the explanation of the user/server acquisition protocol. Therefore, this general description will start with an explanation of the compression-decompression algorithm followed by a discussion of the acquisition protocol and conclude with a more detailed review of the Man-Machine Interface.

2. The Compression-Decompression Algorithm

The goal of the compression-decompression algorithm is to achieve maximal compression ratios but at the same time supply the user with visually adequate interim images. The algorithm should also support loss-less as well as lossy interim and final results, be suited to the medical image processing common to these images and as much as possible be asymmetric and easy to implement using the network computing language.

Figure 4:
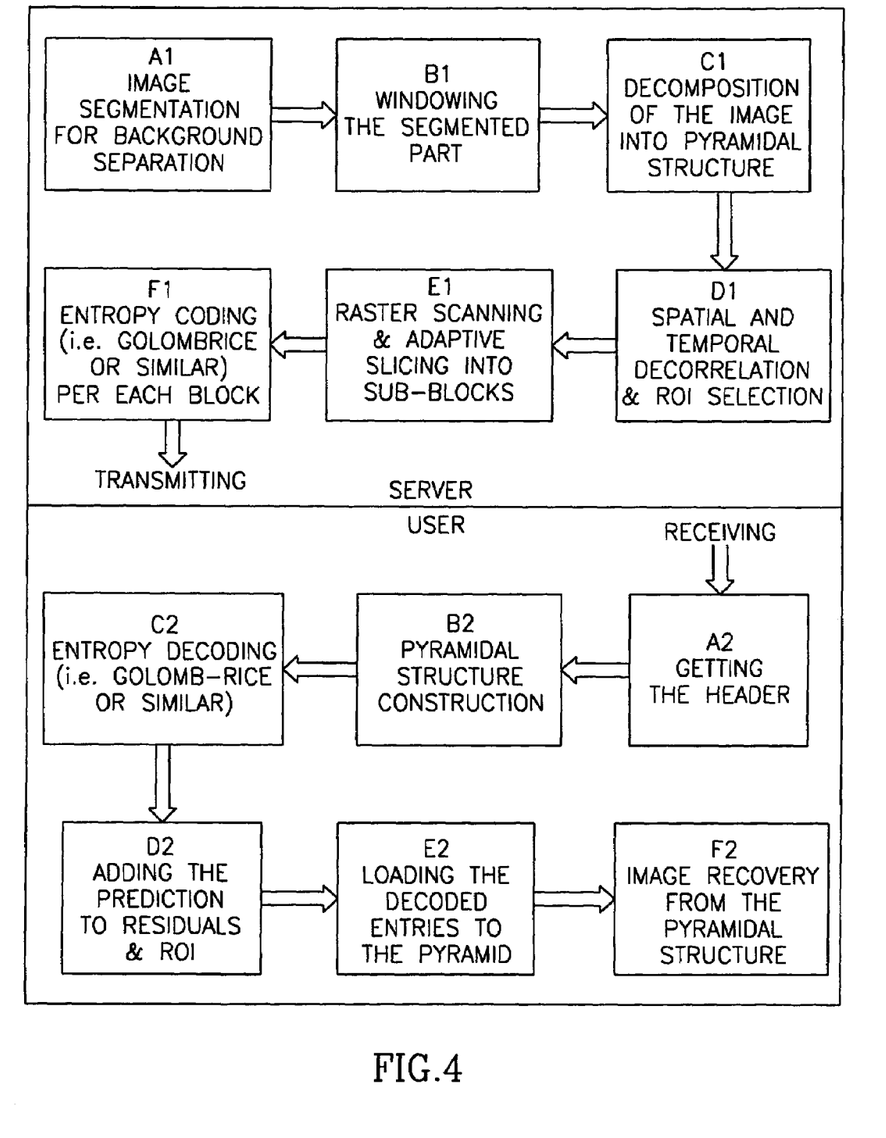
FIG. 4—is a general block diagram of a preferred compression-decompression scheme.

FIG. 4 presents an overview of the compression-decompression algorithm for use with the system described. Compression starts by (optional) segmentation (block A1 in the FIG. 4), where the background of the image (if it exists) is separated from the actual image.

Figure 7A:
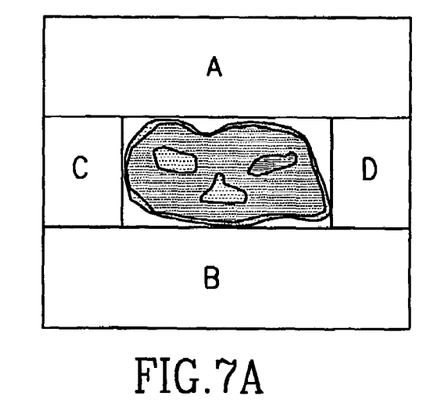
FIGS. 7a and 7b—illustrate the background transmission approach.
Figure 7B:
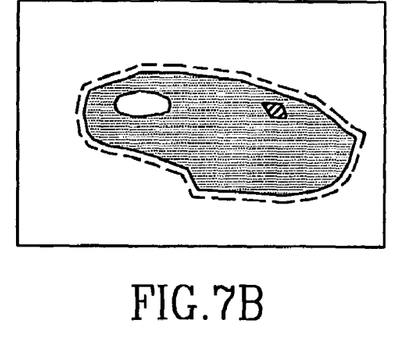

FIGS. 7a and 7b show graphical presentations of such possible background segmentations. The regions denoted A, B, C, and D in FIG. 7a are background regions. The proposed segmentation bounds the region of actual tissue by a rectangle. Only the inner part is progressively transmitted. Other methods of segmentation are possible as shown in FIG. 7b where the actual tissue is shown peripherally bounded by the dashed lines.

The second step (optional) in image coding for compression is a windowing operation (block B1 in FIG. 4), where the dynamic range of the input image is reduced to a lower number of bits per pixel. The new number of bits can represent the client's display capabilities or be derived from the communication bandwidth restrictions. The windowing operation could be done, for example, by estimating the average M and the standard deviation S of the image values, and rescaling these values in the range [(M−S/2) . . . (M+S/2)] using the required new number of bits. As an alternative, an improved locally adaptive windowing method can be applied, which estimates the mean and standard deviation locally. Other well known windowing procedures can be used.

Figure 5:
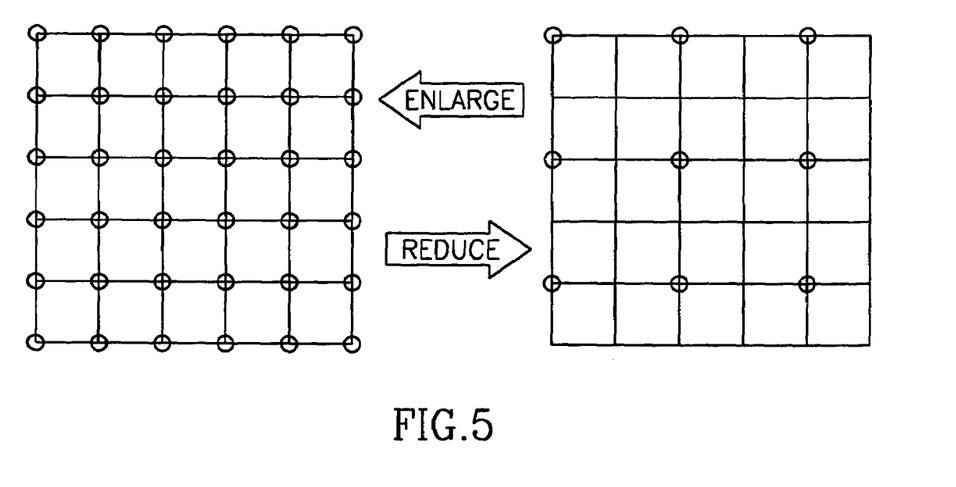
FIG. 5—is a showing of the reduce and enlarge operations in the pyramidal decomposition.
Figure 6:
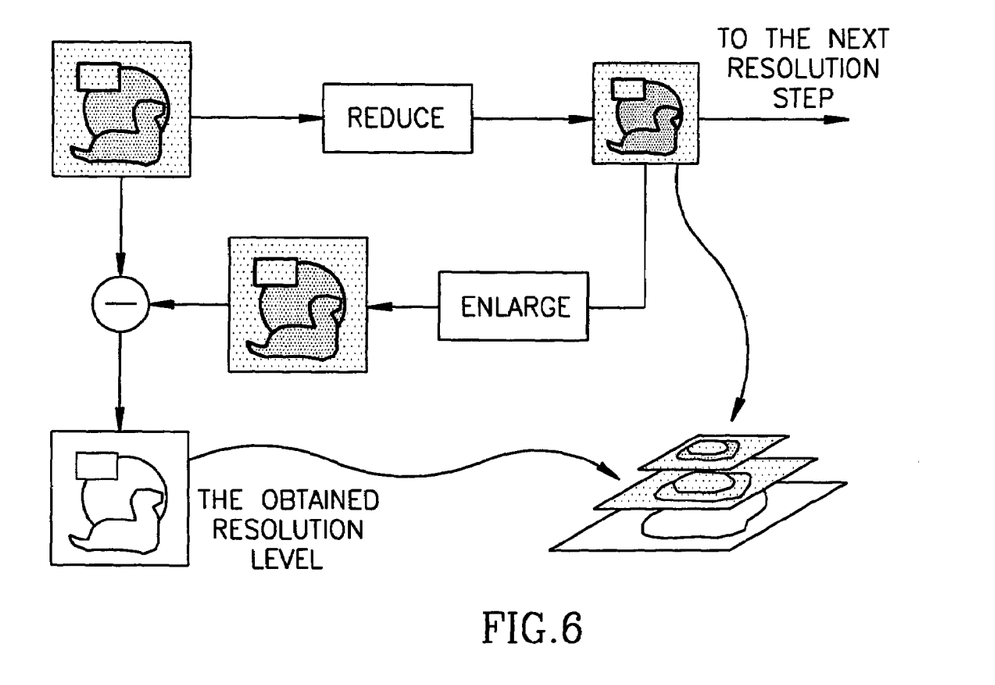
FIG. 6—is a showing of the pyramidal structure concept.

Since one of the goals to be accomplished is to supply the user with meaningful interim results, the medical images are sent progressively. This requirement in turn implies that a pyramidal re-structuring of the image is required (block C1 in FIG. 4). The concept of pyramidal decomposition of an image is shown in FIG. 6, where the two basic operations —Reduce and Enlarge—are further described in FIG. 5. The reduce operation revises or decomposes the image by, for example, simply discarding all even rows and columns, creating an array that is a quarter of the original size. The enlarge operation, for example, bilinearly interpolates the image, resulting in an array four times larger. The interpolation process is not limited to a bilinear interpolation. The exact type of interpolation is selected based on the user's computational and display capabilities. The pyramidal structure contains at the zero-level one small image with reduced resolution. All the remaining levels contain residual values with increased resolution. The pyramidal decomposition of the image could also be achieved through the use of other pyramidal decomposition algorithms. The pyramidal data structures consist of several versions of the original image. Each version is of different size and nature. The pyramidal information is ordered such that the top of the pyramid is the version of the original image which least resembles the original image. If the pyramid is loss-less the final level of the pyramid is an exact replication of the original image. It is clear that after decompressing a specific level we can reconstruct the image up to that level and get an interim result. This interim result resembles the original image according to the level of the pyramid.

Figure 9A:
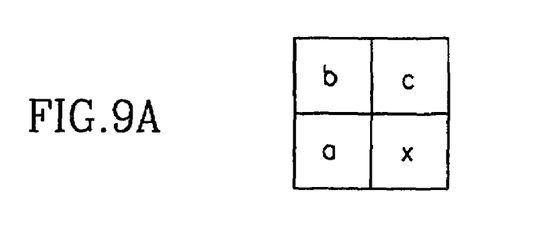
FIG. 9a—illustrates a predictor for a single image.

In order to facilitate an efficient coding scheme, further decorrelation of the data is required. This is achieved by spatial and temporal decorrelation operation (block D1 in FIG. 4). At this stage, each pixel in the current resolution level is predicted by its spatial casual (already transmitted) neighbors. If groups of images are being coded together, temporal neighbors from previous images are used to compute a second predictor, and the best predicator is chosen for each block of pixels. At the end of the prediction stage, the residuals are rescanned into a vector. If the user selected only part of the image to be transmitted (ROI—Region of Interest) only that part of the residual image is scanned and the ROI parameters are added to the header of the image Following is an example of a predictor for a single image (FIG. 9a):

$$x = f(a, b, c) = \begin{cases} \max(a, b) & c < \min(a, b) \\ \min(a, b) & c > \max(a, b) \\ a+b+c & \text{otherwise} \end{cases}$$

Figure 9B:
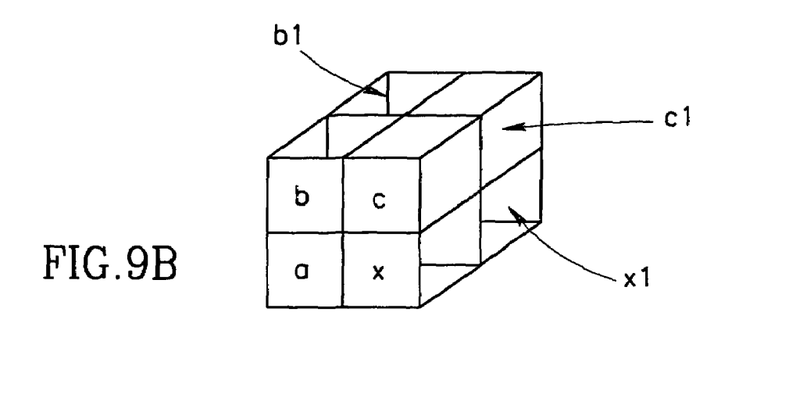
FIG. 9b—illustrates a predictor for a group of images.

Using similar reasoning a predictor for a group of images can be effective in case there is correlation between successive images (FIG. 9b):

x=f(a, b, c, a1, b1, c1, x1)

Figure 10:
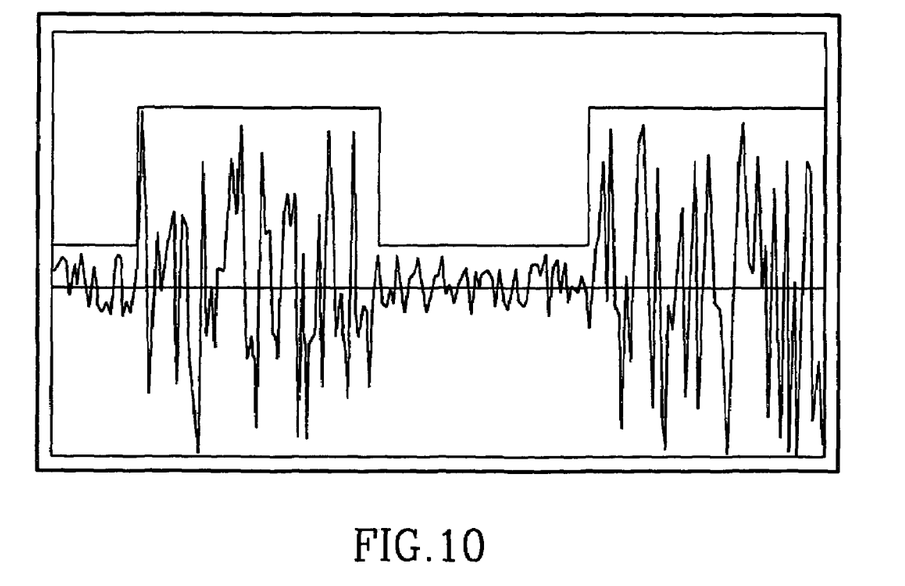
FIG. 10—illustrates an example of vector partitioning.

The residual vector, is partitioned into variable length sub-vectors with a relatively homogeneous probability distribution function (block E1 in FIG. 4). The adaptive partitioning is accomplished by estimating the local mean and variance on the vector, and sectioning the vector on high transients. Each sub-vector is then coded using an entropy coder. One example of such coding is a Golomb-Rice code (block F1 in FIG. 4). An example of a possible partitioning is shown in FIG. 10.

The decompression algorithm is basically the compression operations in inverse order. First, a header is obtained, stating whether segmentation and/or windowing operations were applied, the size of the images and their number, the pyramid depth, etc. (block A2 in FIG. 4). A zeros pyramid is then constructed in order to be filled during the decoding process (block B2 in FIG. 4). Each sub-sector is decoded using inverse entropy coding, i.e., Golomb-Rice code (block C2 in FIG. 4), and all these sub-blocks are rearranged into matrix form. The spatial/temporal prediction is then computed and added to the residuals (block D2 in FIG. 4), and the obtained values are loaded into the pyramid (block E2 in FIG. 4). The pyramid can be restructured to an image at any time during this operation, yielding the obtained image so far.

If segmentation is applied, the background will be transmitted at the end of the transmission of the inner image part. This is for loss-less transmission. For lossy transmission the user can stop the transmission, thus disregarding the background. Transmitting the background is supported by dividing the background into four parts as indicated in FIG. 7a or by mapping the image as indicated in FIG. 7b. Each such part is raster scanned into a vector and the same coding operations presented above apply again, namely, decorrelation, adaptive sectioning, and entropy coding (i.e., Golomb-Rice coding). Other compression-decompression methods of course can be applied within the scope of this invention.

If windowing is applied, the received image at the user's location is a lossy representation of the original image. Upon the user's request, the error image (the difference between the original and the windowed image) should be coded and transmitted. This error image is coded using the same methodology as presented for the background transmission—decorrelation, adaptive sectioning, and entropy coding (i.e., Golomb-Rice coding).

Figure 8:
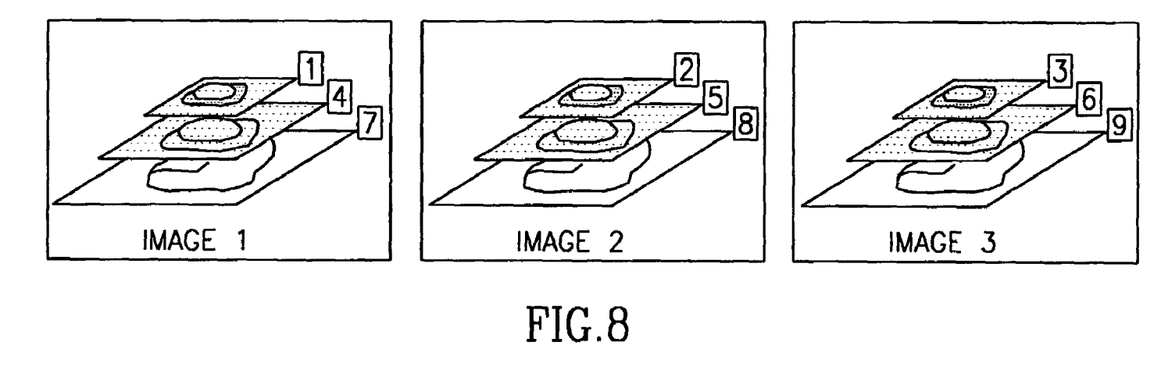
FIG. 8—illustrates the order of transmission.

For image group/series, the order of transmission is as shown in FIG. 8. First, all the low-resolution levels are sent. At the end of this stage, the client may view all the required images in an overview form using the basic version of the entire image set. At the second stage, each of the images is updated by sending the next resolution level. As soon as a resolution level for a specific image is received, the image can be updated to the next interim version which is better than the current version. After several such steps, the images are obtained in error-less form on the user's display Another option, instead of the loss-less entropy coding described above, may be implemented by applying the already existing JPEG routines within the browser software. This approach consists of optional (as before) windowing and/or segmentation steps, followed by a pyramidal decomposition of the obtained image. Each resolution level is then compressed using the lossy JPEG algorithm. At the user, each such level is decompressed accordingly. Since lossy compression-decompression results in deeper compression ratios, and since the decompression routines are written in the computer native language, much shorter waiting periods are obtained at the user's end. As described in detail for the windowing and segmentation operations, one final step of residuals transmission is required in order to support final loss-less representation of the original images at the user's workstation.

In addition to the above described techniques, other methods can be applied within the scope of the present invention. All the above are examples of the invention, which is not limited to those methods.

3. Image Acquisition Process—"Stamps"

Using the insight gained in the explanations rendered until now, the image acquisition process itself can now be described in greater detail. As presented herein above, the user defines the specific medical case (patient, study, series, images) of interest through the use of network application queries into the server's database. Selecting the case is done using the case identifiers which are usually, but not limited to, text or image icons. A typical CT case may contain 50–100 medical images. Out of all these images the goal is to supply the user with the images really needed for the purpose of drawing conclusions (diagnostic, second opinion, etc.) as fast as possible. Usually, out of the entire image case the user will require only a limited number of images and only a specific region of interest (ROI) in the limited number of images. Typically these requirements are case dependent and the user cannot decide which images and what part of these are really needed until the images are viewed. The protocol thus should let the user specify these requirements as soon as possible by supplying the user with interim information which will arrive fast and be sufficiently adequate to make these decisions.

Upon selection of the medical image case the server starts to prepare (as an option) a very basic version of the entire medical case. This basic version of the images will be referred to as "stamps" or icons and will consist of a reduced version, which is visually similar, for every image in the case. The size, in bits, of these "stamps" is small compared with the size of the original images. The entire "stamp" collection is thus a reduced representation of the entire image case. Its size is selected to enable the user to visually select which images are of interest while retaining the small total size. This will assure that the entire reduced representation of the image case will arrive at the user in a relatively short time. Having presented the entire "stamp" collection to the user, the server awaits the user selection of a sub-set of the entire image case. The sub-set can include the entire case but will typically include only several images. This sub-set of the image case will be referred to hereinafter as the "image group". In place of the icons, text can be used to describe the images.

After the user selects the image group, the server prepares a pyramidal decomposition for each and every image in the group or volume process for the whole series. If segmentation and/or windowing were selected, the server performs these operations at this stage. It then goes on and performs the rest of the compression chain (D1 through F1 in FIG. 4) for the top level of the pyramid. This level is the most reduced version of the image and thus is also the smallest. As an option, the server can utilize the "icons" which have been prepared in the previous stage for this purpose. Optionally, as a first stage, only the smallest representation of the image is sent from the server to the user. The user receives and displays the images. After, or even during, this recuperation stage the user can select either a smaller sub set of the group images and/or smaller region of interest out of the image space. This serves as a finger query into the entire image data base and is sent from the user to the server over the communication line. If no finer selection is required the user is enabled to specify whether the visual level obtained so far is sufficient, thus ending the image acquisition process. However, if a better visual level is needed the acquisition process is combined to obtain the next level in the pyramid. Alternatively if the user does nothing the next level is sent. As soon as the server gets the request it performs blocks D1 through F1 on the next level in the pyramid. This is done only to those images which are required and within these images only to that part of the image which is of interest (the ROI). Within the image group the order of compression and communication is presented in FIG. 8. The protocol preferably works on a resolution first basis. All the images in the image group may be brought to the same resolution level and only then the server advances to the next resolution level. Other orders of operation can be used without losing the generality of the invention.

The above process is iterated for all resolution levels. The process is stopped either when the user indicates that the visual level is adequate or the entire image has been sent resulting in a perfect, loss-less, replication of the original image on the user's screen.

The type of temporal prediction, (block D1 in FIG. 4) is selected by the server according to the user's computational capabilities.

If segmentation and/or windowing and/or lossy compression was performed on the images, the user can request the server to complete the images to their loss-less representation. In such a case, the server will compress and transmit the needed information for the user to complete the images to their loss-less version.

At each and every stage the user can choose to broaden the information query requirements, for example, by enlarging the number of images rather than reducing it. In that case, the server will "backtrack" and send the required information to the user.

When the needed information has arrived and been presented to the user, the user is presented with the option to acquire another medical image case from the server.

4. The Man-Machine-Interface

The man-machine interface (MMI) of the user serves as the means by which the user interacts with the system and as a display surface for the medical images. Being a medical images communication network based system, the MMI combines the known and familiar user interface environment of communication software with the tools needed for medical image processing. The goal is to give the user the tools to be part of the described image acquisition process as well as to enable the user to perform tasks regarding the medical image information. The MMI should achieve these goals with minimal to zero intervention or requirements of the user. For that end the entire user software is completely downloaded from the server to the user's machine and for the most part uses part of the communication software already part of the user's machine. All this is done without any user intervention. This also makes user software updates and improvements irrelevant to the end-user. The user software relies heavily on the communication software (e.g. browser) already installed on the user's machine. This enables the user to operate on different machines with different computational and display capabilities. The first task of the user, upon loading the user software into the user's machine is to automatically profile the machine and the network capabilities. This information is then relayed to the server and is used to select various parameters for the rest of the session. This is done without any user intervention.

The MMI, the user is presented with, contains controls which are part of the image acquisition process as well as typical medical image processing tools. The image acquisition tools include case specification tools, image selection tools, resolution level advancement tools, tools for windowing, zooming, panning, graphics and annotations, CINE, and so on.

At all times, the user has full information as to what part of the entire medical image case is currently being viewed on the user's display screen. This information includes, but is not limited to, image number, resolution level, loss-less indicator, region of interest indication, segmentation and window parameters, and so on. By these, the system makes sure the user is fully aware of what exactly is being presented at all times.

While the invention has been particularly shown and described with reference to preferred embodiments thereof, it is to be understood by those skilled in the art that various changes may be made in form and details without departing from the spirit and scope of the invention as defined in the appended claims.

The invention claimed is:

1. An interactive method for allowing a user to obtain image data for diagnostic purposes from a server having access to stored data, comprising:
    connecting a user's computer to the server over a communication network;
    receiving from the server image reconstruction software for the user's computer;
    requesting specific image data for transmission from the server to the user's computer;
    progressively transmitting the requested specific image data over the network from the server to user's computer; and
    reconstructing a diagnostic quality image, from the progressively received image data, using the reconstruction software on the user's computer,
    wherein progressively transmitting the requested data over the network comprises:
    recomposing the image into a pyramidal structure comprised of layers, said layers ranging sequentially from a layer having the least amount of data to a layer having the most data; and
    transmitting the layers making up the pyramid individually starting with the layer with the least amount of data to enable the user to view a progressively improving image to decide on further transmission of the image,
    further comprising:
    providing a first layer with reduced resolution in the pyramidal structure;
    providing remaining layers that contain residual values with increased resolution;
    progressively receiving the data used to provide images based on the received data of progressively improved resolution; and
    using adaptive slicing and entropy coding and decoding of each slice for progressively transmitting the requested specific image data, wherein said entropy coding generates a residual matrix.

2. A method according to claim 1, comprising image processing said reconstructed image using said reconstruction software on said user's computer.

3. A method according to claim 2, wherein the image reconstruction and processing software comprises application software coded using a device independent network programming language.

4. A method according to claim 1, comprising:
receiving from the server image selection software for the user's computer,
wherein said image selection software is used for said requesting.

5. A method according to claim 4, wherein said image selection software controls the transmission of the image data.

6. A method according to claim 4, wherein said image selection software displays images from said server.

7. A method according to claim 4, wherein said image selection software and said reconstruction software are received together.

8. A method according to claim 4, wherein said image selection software and said reconstruction software comprise a single software unit.

9. A method according to claim 4, wherein said image selection software is operative to stop the transmission of the data, after at least a low quality image is reconstructed and viewed from said data.

10. A method according to claim 9, wherein said image selection software is operative to restart the transmission of the data of the entire image, after said stopping.

11. A method according to claim 4, wherein said image selection software controls processing of data at said server, prior to its transmission.

12. A method according to claim 11, wherein said processing comprises reducing said data from a large bit-per-pixel ratio to a small bit per pixel ratio, independently of details of said request, except an identification of the data requested.

13. A method according to claim 12, wherein reducing the bit-per-pixel ratio comprises:
calculating an average "M" of the gray values in the image and a standard deviation "S" of said gray values; and
rescaling these values in the range [(M−S/2) ... (M+S/2)] to obtain a new lower number of bits per pixel.

14. A method according to claim 12, wherein reducing the bit-per-pixel ratio comprises:
estimating the mean and standard deviation of the gray levels locally; and
rescaling these values to obtain a new lower number of bits per pixel.

15. A method according to claims 11, comprising interactively providing user input to said image selection software, to affect said control.

16. A method according to claim 11, wherein said server processes said image data for enhancing transmission thereof.

17. A method according to claim 4, wherein said image selection software controls said server to selectively transmit only portions of the image data.

18. A method according to claim 4, wherein the image selection software comprises application software coded using a device independent network programming language.

19. A method according to claim 18, wherein said language comprises Java.

20. A method according to claim 18, wherein said language comprises ActiveX.

21. A method according to claim 4, wherein the reconstruction software comprises application software coded using a device independent network programming language.

22. A method according to claim 4, wherein said image selection software controls said server to selectively transmit only a region of interest of said image.

23. A method according to claim 1, wherein reconstructing comprises:
reconstructing images of progressively improving quality from the progressively received data;
using the produced improved images of progressively produced quality to decide on processing of the images, wherein said processing comprises gray-level windowing; and
processing said images, prior to the progressively received data being completely received.

24. A method according to claim 1, wherein reconstructing comprises:
reconstructing images of progressively improving quality from the progressively received data;
using the produced improved images of progressively produced quality to decide on processing of the images; and
interactively selecting regions of interests in the images based on said progressively improved images, prior to the progressively received data being completely received.

25. A method according to claim 1, wherein said data is progressively transmitted while a lower quality image is being reconstructed from said data.

26. A method according to claim 1, wherein reducing comprises discarding alternate rows and columns to create an image that is a quarter of the size of the original image.

27. A method according to claim 1, comprising:
compressing the requested data transmitted over the network; and
decompressing the received required data to provide images.

28. A method according to claim 27, wherein compressing comprises spatially decorrelating the data by predicting each pixel at the current resolution using its spatial casual neighbors.

29. A method according to claim 28, wherein a predictor X used in predicting each pixel value for a single image is equal to f(a, b, c), wherein a, b and c are previously predicted neighboring pixels.

30. A method according to claim 27, wherein compressing comprises temporally decorrelating each pixel by predicting each pixel value at the current resolution using the values of temporal neighbors from previous images.

31. A method according to claim 30, wherein a predictor X used in predicting each pixel value for a group of images equals f(a, b, c, a1, b1, c1, x1) wherein a, b and c are previously predicted neighboring pixels in a same image and a1, b1, c1 and x1 are corresponding pixels in a previously predicted image of the image group.

32. A method according to claim 1, wherein said entropy coding and decoding are accomplished using Golomb Rice entropy coding and decoding.

33. A method according to claim 1, wherein using adaptive slicing comprises:
scanning the obtained residual matrix into a residual vector; and
partitioning the residual vector into variable length sub vectors with a relatively homogeneous probability distribution function.

34. A method according to claim 33, wherein partitioning comprises:
estimating the local mean and variance on the sub-vector;
sectioning the vector on high transients; and
coding each sub vector separately.

35. A method according to claim 33, wherein said compression does not increase the size of said data.

36. A method according to claim 1, wherein connecting the user computer to the server over a communication network comprises connecting over the Internet.

37. A method according to claim 1 wherein connecting the user computer to the server over a communication network comprises using a dial up communication system.

38. A method according to claim 1 wherein connecting the user computer to the server over the communication network comprises using networking facilities.

39. A method according to claim 1, wherein the stored data comprises data for a plurality of "postage stamp" images.

40. A method according to claim 39, comprising using "postage stamp" images as a catalog for selecting those images for which no further data is to be transmitted and those images for which further data is to be transmitted.

41. A method according to claim 39, wherein said postage stamps comprise a lowest level in a pyramidal representation of said images.

42. A method according to claim 1, wherein progressively transmitting comprising transmitting data operative to reconstruct images of increasing resolution.

43. A method according to claim 1, wherein progressively transmitting the requested data over the network comprises segmenting an image into background parts and tissue parts, and transmitting the tissue parts first.

44. A method according to claim 1, wherein said requesting comprises requesting after said receiving and during a same session.

45. A method according to claim 1, wherein said server only transmits image data received from a data store connected to said server by a network connection.

46. A method according to claim 1, wherein said connecting and said receiving are performed via an industry standard browser software.

47. A method according to claim 1, wherein receiving from the server image reconstruction software is performed in each session in which the user receives progressively transmitted images.

48. A method according to claim 1, wherein receiving from the server image reconstruction software is performed after requesting image data by the user.

\* \* \* \* \*